United States Patent
Gopalkrishnan et al.

(10) Patent No.: US 11,235,972 B2
(45) Date of Patent: Feb. 1, 2022

(54) SEQUENCE DESIGN FOR EFFICIENT ASSEMBLY OF NUCLEIC ACID STRUCTURES

(71) Applicant: President and Fellows of Harvard College, Cambridge, MA (US)

(72) Inventors: Nikhil Gopalkrishnan, Jamaica Plain, MA (US); Thomas E. Schaus, Arlington, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 771 days.

(21) Appl. No.: 16/092,802

(22) PCT Filed: Apr. 11, 2017

(86) PCT No.: PCT/US2017/026959
§ 371 (c)(1),
(2) Date: Oct. 11, 2018

(87) PCT Pub. No.: WO2017/180592
PCT Pub. Date: Oct. 19, 2017

(65) Prior Publication Data
US 2019/0169024 A1    Jun. 6, 2019

Related U.S. Application Data (60) Provisional application No. 62/321,146, filed on Apr. 11, 2016.

(51) Int. Cl.
*B82B 3/00* (2006.01)
*C07H 21/04* (2006.01)
*C12Q 1/6811* (2018.01)
*C12N 15/10* (2006.01)
*B82Y 40/00* (2011.01)

(52) U.S. Cl.
CPC .......... *B82B 3/0042* (2013.01); *C07H 21/04* (2013.01); *C12N 15/10* (2013.01); *C12Q 1/6811* (2013.01); *B82Y 40/00* (2013.01); *C12Q 2563/155* (2013.01); *C12Q 2563/157* (2013.01); *C12Q 2565/133* (2013.01)

(58) Field of Classification Search
CPC ..... B82B 3/0042; C12N 15/10; C12Q 1/6811; C07H 21/04; B82Y 40/00
See application file for complete search history.

(56) References Cited

U.S. PATENT DOCUMENTS

| | | | | |
|---|---|---|---|---|
| 8,501,923 B2 * | 8/2013 | Rothemund | ........... | C12N 15/10 536/23.1 |
| 2008/0287668 A1 * | 11/2008 | Toth-Fejel | ............. | C07H 21/04 536/25.3 |
| 2012/0022244 A1 * | 1/2012 | Yin | ........................ | B82Y 40/00 536/23.1 |
| 2014/0031240 A1 * | 1/2014 | Behlke | ................. | C12Q 1/6869 506/2 |
| 2014/0303320 A1 | 10/2014 | Schaus et al. | | |
| 2015/0191719 A1 * | 7/2015 | Hudson | .............. | C12N 15/1031 506/2 |

OTHER PUBLICATIONS

Snodin et al, Direct Simulation of the Self-Assembly of a Small DNA Origami, 2016, ACS Nano, 10, 1724-1737 (Year: 2016).*
Eickert, Using Modular Preformed DNA Origami Building Blocks to Fold Dynamic 3D Structures. Thesis [Online], The Ohio State University, 2014. retrieved online Jun. 11, 2017 @ https://etd.ohiolink.edu/etd.send_file?accession=osu1397742084&disposition=inline. 63 pages.
Jungmann et al., Isothermal assembly of DNA origami structures using denaturing agents. J Am Chem Soc. 2008;130(31):10062-3. Epub Jul. 10, 2008.
Kopielski et al., Isothermal DNA origami folding: Avoiding denaturing conditions for one-pot, hybrid-component annealing. Nanoscale. 2015;7:2102-6. Epub Dec. 3, 2014.
Myhrvold et al., Isothermal self-assembly of complex DNA structures under diverse and biocompatible conditions. Nano Lett. Sep. 11, 2013;13(9):4242-8. Epub Aug. 26, 2013.
Rothemund, Folding DNA to create nanoscale shapes and patterns. Nature. Mar. 2006;440:297-302.
Sobczak et al., Rapid folding of DNA into nanoscale shapes at constant temperature. Science. Dec. 14, 2012;338(6113):1458-61.
Song et al., Isothermal hybridization kinetics of DNA assembly of two-dimensional DNA origami. Small. 2013;9(17):2954-9.
Tsutsumi et al., GENESUS: A two-step sequence design program for DNA nanostructure self-assembly. BioTechniques. Apr. 2014;56(4):180-5.

* cited by examiner

*Primary Examiner* — Narayan K Bhat
(74) *Attorney, Agent, or Firm* — Wolf, Greenfield & Sacks, P.C.

(57) ABSTRACT

The present disclosure provides, in some aspects, methods and compositions for producing nucleic acid nanostructures having little to no kinetic barriers to self-assembly.

14 Claims, 4 Drawing Sheets
Specification includes a Sequence Listing.

SEQUENCE DESIGN FOR EFFICIENT ASSEMBLY OF NUCLEIC ACID STRUCTURES

RELATED APPLICATIONS

This application is a national stage filing under 35 U.S.C. § 371 of international application number PCT/US2017/026959, filed Apr. 11, 2017, which claims the benefit under 35 U.S.C. § 119(e) of U.S. provisional application No. 62/321,146, filed Apr. 11, 2016, each of which is incorporated by reference herein in its entirety.

FEDERALLY SPONSORED RESEARCH

This invention was made with government support under Contract No. EB018659 awarded by National Institutes of Health, under Grant Nos. 1540214 and 1317291 awarded by National Science Foundation, and under Contract Nos. N00014-13-1-0593 and N00014-14-1-0610 awarded by United States Department of Defense Office of Naval Research. The government has certain rights in the invention.

BACKGROUND

Deoxyribonucleic acid (DNA) origami is the nanoscale folding of DNA to create non-arbitrary two-dimensional and three-dimensional shapes at the nanoscale. The specificity of the interactions between complementary base pairs make DNA a useful construction material, through design of its base sequences. The conventional DNA origami process involves the folding of a long single strand of viral DNA (often referred to as a "scaffold" strand) aided by multiple shorter "staple" strands. These shorter staple strands bind the longer scaffold strand in various places, resulting in various shapes. Thus, the sequence of a staple strand is determined by the sequence of the scaffold strand to which it binds. DNA nanostructures have been widely utilized in material science, synthetic biology, biological imaging, structural determination, and drug delivery.

SUMMARY

Provided herein, in some embodiments, are compositions and methods that permit efficient isothermal self-assembly of non-arbitrary nucleic acid (e.g., DNA) nanostructures at a wide range of temperatures, including at physiological temperature and room temperature. Self-assembly of nanostructures, as provided herein, relies, at least in part, on minimizing or eliminating kinetic barriers that often hinder the nucleic acid self-assembly process by introducing secondary structure, intramolecular nucleic acid interactions (e.g., hybridization between subsequences within the same scaffold strand) and unintended intermolecular nucleic acid interactions (e.g., hybridization between staple strands).

A contributing kinetic barrier to nucleic acid nanostructure self-assembly (e.g., at room temperature) includes (i) secondary structure of the nucleic acid scaffold strand and nucleic acid staple strands, (ii) intermolecular staple-staple interactions and (iii) unintended intermolecular staple-scaffold interactions. Secondary structure occurs when two complementary or near-complementary regions within a nucleic acid strand hybridize, even transiently, to each other to form loops, duplexes, hairpin structures, three-way structures, four-way structures, or any other structure. Intermolecular interactions occur when two complementary or near-complementary regions across two or more nucleic acid strands hybridize, even transiently, to each other to form loops, duplexes, hairpin structures, three-way structures, four-way structures, or any other structure. The present disclosure demonstrates that secondary structure and undesired/unintended intermolecular interactions may be minimized or eliminated by rationally designing the nucleotide sequence of the strands to minimize or eliminate one of the four nucleotides (e.g., A, T, C or G) and to minimize or eliminate repeat subsequences. A nucleic acid strand having a 3-letter code favors a linear arrangement, in part because there is one less binding partner facilitating intramolecular binding (e.g., without a G, C cannot pair with another nucleotide within the strand). Two or more nucleic acid strands having a 3-letter code are also less likely to have intermolecular interactions because there is one less binding partner facilitating intermolecular binding. Minimizing repeated subsequences helps to prevent unintended intermolecular interactions by increasing the likelihood that complementary subsequences occur only where intended and are not present elsewhere in the scaffold strand.

Thus, nucleic acid "scaffold" and "staple" strand sequences of the present disclosure have primarily three different types of nucleotides (e.g., A, T and C, or A, T and G), thus minimizing secondary structure formation and intermolecular staple-staple interactions. Also, nucleic acid "scaffold" and "staple" strand sequences of the present disclosure are rationally designed to minimize sequence repeats, thus minimizing unintended scaffold-staple interactions. A nucleic acid "scaffold" strand is typically a strand of nucleotides having a length of greater than 100 nucleotides. By contrast a nucleic acid "staple strand" is typically a strand of nucleotides having a length of 100 nucleotides or less. It should be understood that the lengths of scaffold strands and complementary staple strands may vary, as long as the scaffold strand is longer than the staple strands. Thus, a scaffold strand may be shorter than 100 nucleotides, provided the scaffold strand is longer than complementary staple strands. Likewise, the staple strands may be longer than 100 nucleotides, provided the staple strands are shorter than a complementary scaffold strand (a strand that contains subsequences that are complementary to the staple strands).

In some embodiments, the GC content of nucleic acid scaffold and staple strands is minimized to reduce the strength of secondary structure and intermolecular staple-staple base pairing. G and C nucleotides form a 3-hydrogen bond when paired together, whereas A and T nucleotides form a weaker 2-hydrogen bond. Reducing or eliminating G-C binding weakens the strength of undesired interactions (e.g., via base pairing). Thus, nucleic acid scaffold strands, in some embodiments, have a nucleotide sequence (e.g., full-length sequence) that comprises less than 10% (e.g., less than 9, 8, 7, 6, 5, 4, 3, 2 or 1%) of one of C, G, T or A nucleotides. For example, at least 90% of the nucleotides of a nucleic acid scaffold strand may be comprised of a combination of A, T and C, while less than 10% (e.g., less than 5%) of the nucleotides of the nucleic acid scaffold strand may be comprised of G. As another example, at least 90% of the nucleotides of a nucleic acid scaffold strand may be comprised of a combination of A, T and G, while less than 10% (e.g., less than 5%) of the nucleotides of the nucleic acid scaffold strand may be comprised of C.

Moreover, nucleic acid scaffold and staple sequences have minimal sequence repeats. This design also minimizes or eliminates unintended intermolecular scaffold-staple base pairing and, thus, kinetic traps.

Figure 1:
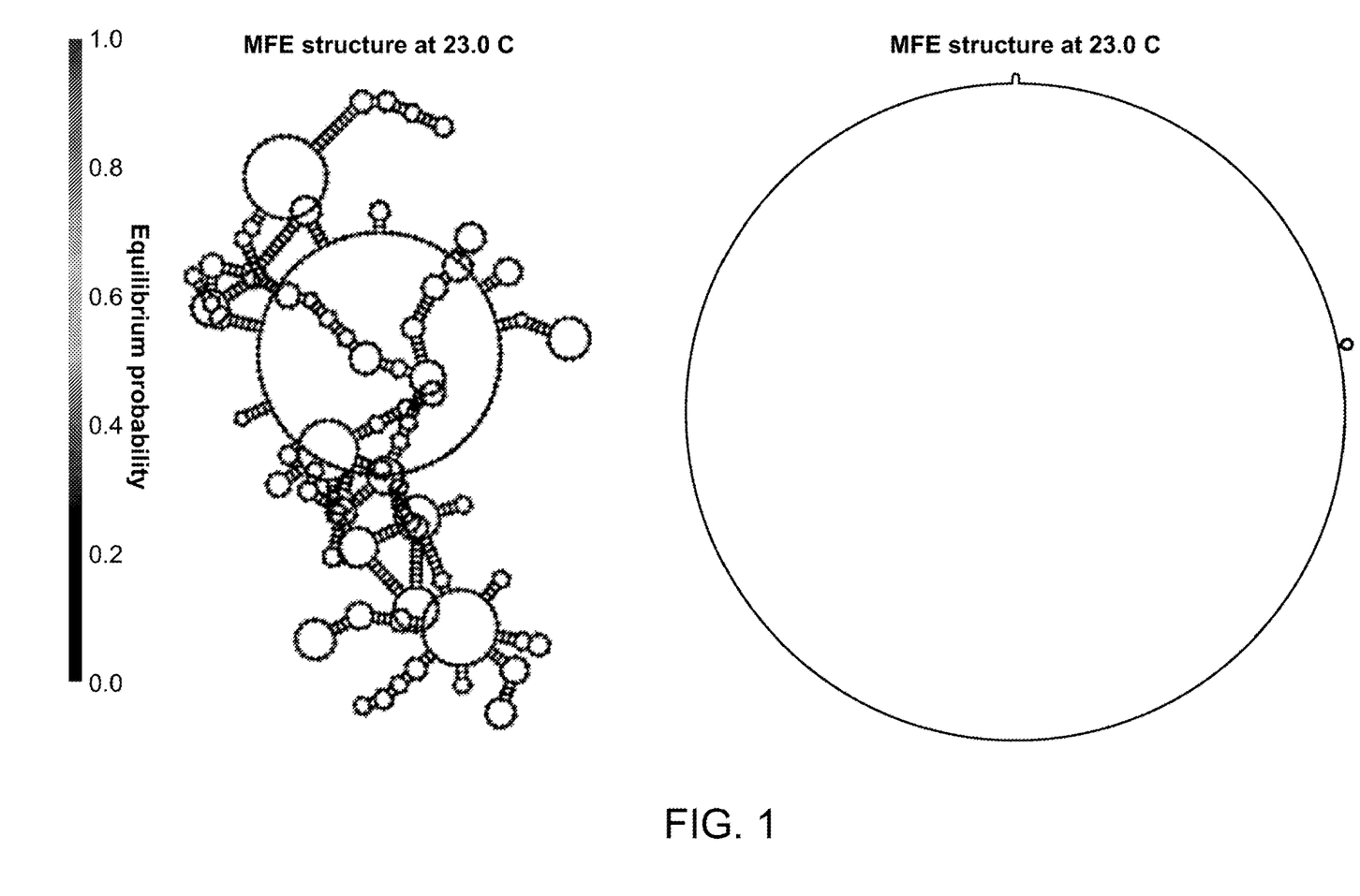
FIG. 1 shows a random 1000 base four letter scaffold sequence (left) with significant secondary structure, while a three letter scaffold sequence (right) shows almost no secondary structure under the same conditions. The free energies of the two secondary structures are −165.53 kcal/mol and −0.77 kcal/mol, respectively. The scaffolds were analyzed with NUPACK, an online tool for analyzing nucleic acid thermodynamics.

FIG. 1 shows a comparison of secondary structures formed from a 1000-nucleotide scaffold strand having a conventional 4-letter (A, T, C, G) code (left) and a 1000-nucleotide scaffold strand having a 3-letter (e.g., A, T, C) code (right). The scaffold strand having a 3-letter code exhibits little to no secondary structure.

Figure 2:
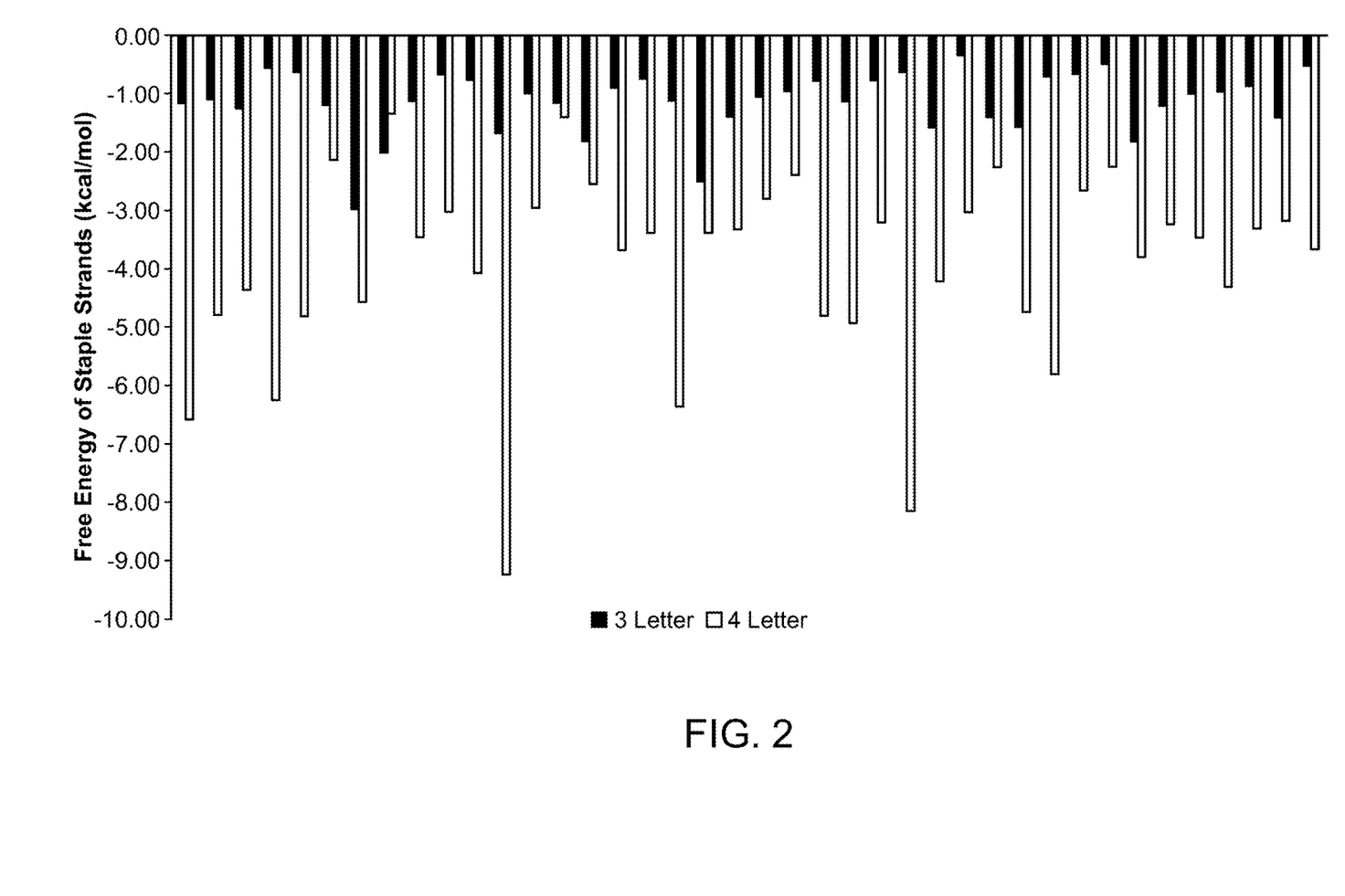
FIG. 2 shows a comparison of secondary structure for corresponding sets of staple strands. The staple strands corresponding to a 4-letter (A, T, C, G) code are themselves 4-letter sequences (A, T, C, G) and exhibit significant secondary structure (as signified by a more negative free energy). The staple strands corresponding to a 3-letter code (A, T, C) are themselves 3-letter sequences (A, T, G) and exhibit little to no secondary structure (as signified by less negative free energy).

FIG. 2 shows a comparison of secondary structure for corresponding sets of staple strands. The staple strands corresponding to a 4-letter (A, T, C, G) code are themselves 4-letter sequences (A, T, C, G) and exhibit significant secondary structure (as signified by a more negative free energy). The staple strands corresponding to a 3-letter code (A, T, C) are themselves 3-letter sequences (A, T, G) and exhibit little to no secondary structure (as signified by less negative free energy).

Figure 3:
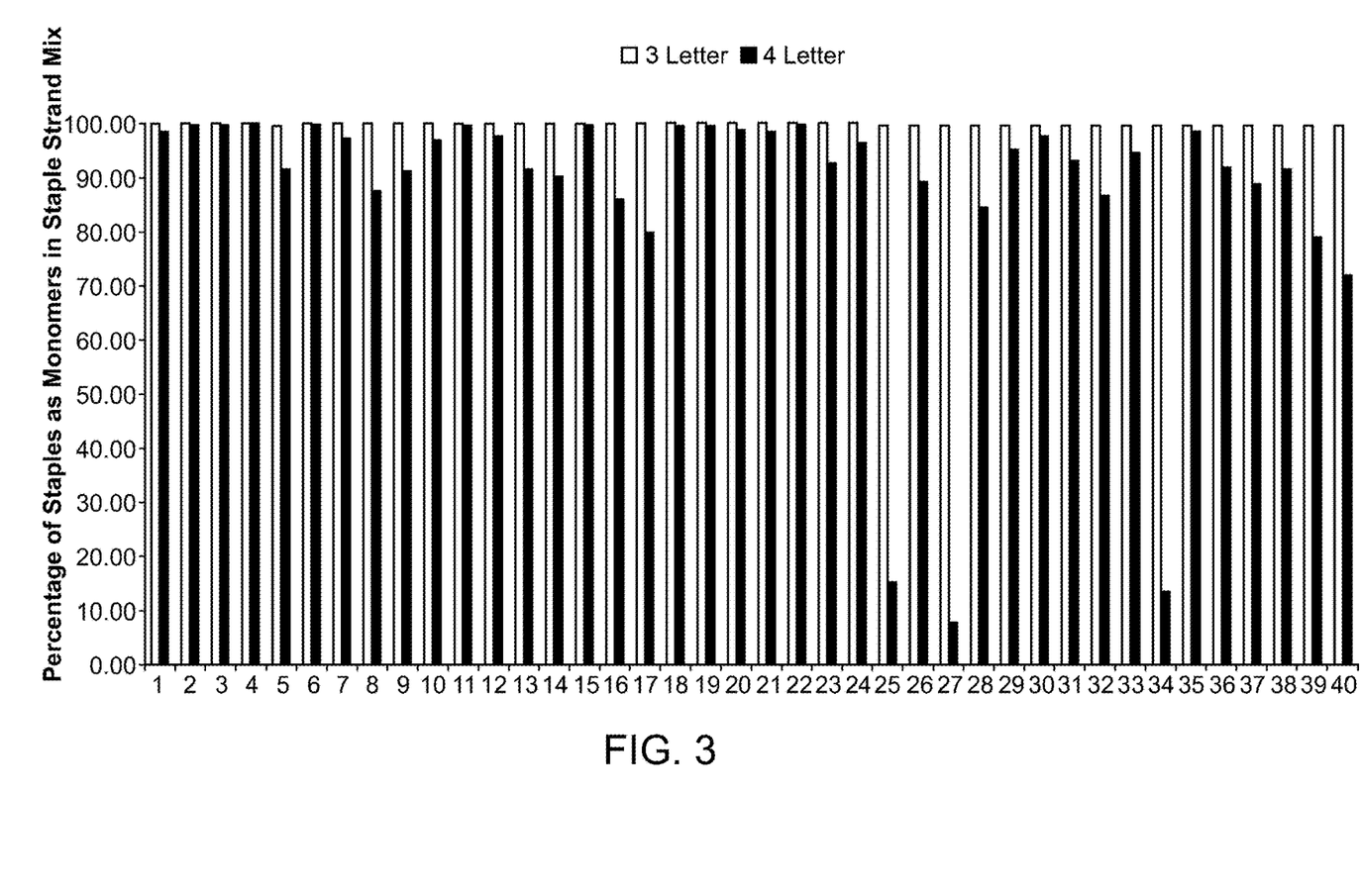
FIG. 3 shows a comparison of staple-staple interactions for corresponding sets of staple strands. Some of the staple strands corresponding to a 4-letter (A, T, C, G) code have significant undesired staple-staple interactions (signified by a low percentage of the staple strands as monomers in solution). The staple strands corresponding to a 3-letter code (A, T, C) are themselves 3-letter sequences (A, T, G) and exhibit little to no undesired staple-staple interactions (signified by a high (close to 100%) percentage of the staple strands as monomers in solution).

FIG. 3 shows a comparison of staple-staple interactions for corresponding sets of staple strands. Some of the staple strands corresponding to a 4-letter (A, T, C, G) code have significant undesired staple-staple interactions (signified by a low percentage of the staple strands as monomers in solution). The staple strands corresponding to a 3-letter code (A, T, C) are themselves 3-letter sequences (A, T, G) and exhibit little to no undesired staple-staple interactions (signified by a high (close to 100%) percentage of the staple strands as monomers in solution).

Also provided herein are engineered nucleic acid scaffold strands having a length of at least 100 nucleotides and having a nucleotide sequence that comprises less than 10% of one of C, G, T or A nucleotides.

In some embodiments, a nucleic acid scaffold strand comprises greater than 90% (e.g., 95% or 98%) of A, T/U and C nucleotides and less than 10% (e.g., 5% or 2%) of G nucleotides. In some embodiments, a nucleic acid scaffold strand comprises greater than 90% of A, T/U and G nucleotides and less than 10% of C nucleotides. In some embodiments, the nucleic acid scaffold strand comprises a nucleotide sequence comprising 1-5% of one of C, G, T or A nucleotides. In some embodiments, the nucleic acid scaffold strand consists of: A, T and C; A, T and G; A, G and C; or T; G and C.

In some embodiments, the nucleic acid scaffold strand comprises nucleotide subsequences (contiguous sequences shorter than the full-length sequence), each of which is present only once (is not repeated) in the nucleic acid scaffold strand. In some embodiments, the nucleic acid scaffold strand comprises nucleotide subsequences, wherein any subsequence is repeated, if at all, only 1, 2 or 3 times.

In some embodiments, the nucleic acid scaffold strand has a length of at least 500 nucleotides. For example, a nucleic acid scaffold strand may have a length of at least 1000 nucleotides. In some embodiments, the nucleic acid scaffold strand has a length of at least 100-100,000 nucleotides. In some embodiments, the nucleic acid scaffold strand (and the nucleic acid nanostructure) is DNA. In some embodiments, the nucleic acid scaffold strand (and the nucleic acid nanostructure) is RNA or a combination of DNA and RNA.

In some embodiments, the nucleic acid nanostructure comprises a plurality of oligonucleotides (referred to herein as "staple" strands). For example, a nucleic acid nanostructure may include 10-2000 oligonucleotides (e.g., DNA oligonucleotides). In some embodiments, the oligonucleotides have a length of 5 to 10 nucleotides, or a length of 3 to 30 nucleotides.

In some embodiments, a nucleic acid scaffold strand has a C-content or G-content of 20%-60% (e.g., 20%, 25%, 30%, 35%, 40%, 45%, 50%, 55% or 60%) for each subsequence having a length of at least 10 nucleotides (e.g., at least 15, at least 20, at least 30, at least 35, at least 40, at least 45 or at least 50 nucleotides).

In some embodiments, the nucleic acid nanostructure is two-dimensional or three-dimensional. In some embodiments, the nucleic acid nanostructure has a diameter of 10-500 nm.

Other aspects of the present disclosure provide a kit comprising (a) a nucleic acid strand having a length of at least 100 nucleotides and having a nucleotide sequence that comprises less than 10% of one of C, G, T or A nucleotides; and (b) a plurality of oligonucleotides, wherein each oligonucleotide is at least partially complementary to and at least partially bound to the nucleic acid strand. In some embodiments, the kit further comprising buffer supplemented with monovalent cations and/or divalent cations.

Still other aspects of the present disclosure provide a method of producing a nucleic acid nanostructure, comprising incubating, in a reaction vessel, (a) a nucleic acid strand having a length of at least 100 nucleotides and having a nucleotide sequence that comprises less than 10% of one of C, G, T or A nucleotides, and (b) a plurality of oligonucleotides, wherein each oligonucleotide is at least partially complementary to the nucleic acid strand, under conditions that result in binding of the oligonucleotides to the nucleic acid strand to form a nucleic acid nanostructure. In some embodiments, the method comprises conditions including incubating a nucleic acid strand and a plurality of oligonucleotides in a buffer at a temperature of 4-70° C. for at least 5 minutes.

DESCRIPTION

Nucleic acid nanostructure self-assembly using, for example, a conventional origami approach (Rothemund,

*Nature* 440 (7082): 297-302), typically requires annealing of nucleic acid strands at high temperature (e.g., >80° C.), which are not always compatible with temperature-sensitive components or contexts.

Provided herein are compositions and methods for self-assembly of nucleic acid (e.g., DNA) nanostructures at a wide range of temperatures, including at physiological temperature and room temperature). Self-assembly of nanostructures, as provided herein, relies, in part, on minimizing or eliminating kinetic barriers such as undesired secondary structure, undesired intermolecular nucleic acid interactions (e.g., staple-staple interactions) and unintended intermolecular nucleic acid interactions (e.g. staple-scaffold interactions) that often hinder the self-assembly process. Nucleic acid sequences of the present disclosure are engineered to minimize or eliminate secondary structure and undesired/unintended intermolecular base pairing, thereby facilitating self-assembly. More specifically, nucleic acid sequences disclosed herein have primarily three different types of nucleotides (e.g., A, T and C, or A, T and G) and have minimal sequence repeats.

Nucleic Acid Strands

Some aspects of the present disclosure provide engineered nucleic acid strands (e.g., scaffold strands and staple strands) that self-assemble in a pre-determined matter to form a nucleic acid nanostructure.

Kinetic barriers to nucleic acid self-assembly are minimized or eliminated by engineering a nucleic acid strand in a way that minimizes or eliminates secondary structure formation and undesired/unintended intermolecular interactions. The present disclosure includes varying the percentage of C, G, T or A nucleotides in an engineered nucleic acid strand to minimize or eliminate kinetic barriers to self-assembly. The percentage of C, G, T or A nucleotides with reference to a nucleic acid scaffold strand refers to the percentage of that nucleotide in the entirety) full length of the strand. Percent nucleotide composition may also be defined in the context of subsequences. Thus, particular subsequences (sequences shorter than the full length sequence) may contain a particular percentage of one or more nucleotide types (e.g., A particular percentage of A, T or C/G, or a particular percentage of a combination of A, T and C/G.) "C/G" refers to C or G.

In some embodiments, the engineered nucleic acid strand has a length of at least 100 nucleotides and has a nucleotide sequence that comprises less than 10% of one of C, G, T or A nucleotides. For example, a nucleic acid scaffold strand may be primarily composed of A, T and C nucleotides and contain only a few G nucleotides. Thus, in some embodiments, the engineered nucleic acid strand comprises greater than 90% (e.g., greater than 95%) of A, T/U and C nucleotides and less than 10% (e.g., less than 5%) of G nucleotides. In some embodiments, the engineered nucleic acid strand comprises greater than 90% (e.g., greater than 95%) of A, T/U and G nucleotides and less than 10% (e.g., less than 5%) of C nucleotides. In some embodiments, the engineered nucleic acid strand comprises greater than 90% (e.g., greater than 95%) of A, C and G nucleotides and less than 10% (e.g., less than 5%) of T nucleotides. In some embodiments, the engineered nucleic acid strand comprises greater than 90% (e.g., greater than 95%) of T, C and G nucleotides and less than 10% (e.g., less than 5%) of A nucleotides.

The engineered nucleic acid strand percentages are not limited to less than 10% of one of C, G, T, or A nucleotides. In some embodiments, the engineered nucleic acid strand comprises less than 5% of one of C, G, T or A nucleotides. In some embodiments, the engineered nucleic acid strand comprises 1-5% (e.g., 1%, 2%, 3%, 4% or 5%) of one of C, G, T or A nucleotides.

The present disclosure includes minimizing subsequence repeats in the engineered nucleic acid strand sequence to minimize or eliminate kinetic barriers to self-assembly. Despite reduced sequence diversity of a nucleic acid strand comprising three different nucleotides compared to a nucleic acid strand comprising four different nucleotides, many distinct nucleotide sequences may be generated. For example, a nucleotide sequence having a length of 8 and consisting of 3 different nucleotides yields ~6500 ($3^8$=~6500) distinct nucleotide sequences that may occur in the nucleic acid strand. A nucleotide sequence having a length of 8 and consisting of 4 different nucleotides yields ~65000 ($4^8$=~65000) distinct nucleotide sequences that may occur in the nucleic acid strand.

A "subsequence" refers to a discrete, contiguous sequence of nucleotides or nucleotide base pairs, depending on whether the domain is unpaired (single-stranded nucleotides) or paired (double-stranded nucleotide base pairs), respectively. One subsequence is "complementary to" another subsequence if one subsequence contains nucleotides that base pair (hybridize/bind through Watson-Crick nucleotide base pairing) with nucleotides of the other subsequence such that the two subsequences form a paired (double-stranded) or partially-paired molecular species/structure. In some embodiments, a subsequence in a first nucleic acid strand is described as "complementary to" a subsequence in a second nucleic acid strand such that, by pairing up complementary regions, the nucleic acid strand becomes double-stranded. In some embodiments, a subsequence in the nucleic acid strand is described as "complementary to" an oligonucleotide such that, by pairing up complementary regions, the DNA assembles into a pre-defined nanostructure. Complementary subsequences need not be perfectly (100%) complementary to form a paired structure, although perfect complementarity is provided, in some embodiments.

In some embodiments, a nucleic acid strand sequence comprises nucleotide subsequences, each of which is present only once (or up to twice or up to three times) in a nucleic acid scaffold strand. In some embodiments, subsequences have a length of 3 to 50 nucleotides. For example, subsequences may have a length of 3-40, 3-30, 3-20, 3-10, 5-50, 5-40, 5-30, 5-20, or 5-10 nucleotides.

In some embodiments, a nucleic acid strand comprises a nucleotide subsequence having a length of 3 to 30 nucleotides. In some embodiments, the engineered nucleic acid strand comprises a nucleotide subsequence having a length of 3 to 35 nucleotides, 3 to 40 nucleotides, 3 to 45 nucleotides, 3 to 50 nucleotides, 3 to 100 nucleotides, or 3 to 200 nucleotides. In some embodiments, the engineered nucleic acid strand comprises a nucleotide subsequence having a length of 3 to 25 nucleotides, 3 to 20 nucleotides, 3 to 15 nucleotides, 3 to 10 nucleotides, or 3 to 5 nucleotides. In some embodiments, the engineered nucleic acid strand comprises a nucleotide subsequence having a length of 4 to 11 nucleotides, 4 to 10 nucleotides, 4 to 9 nucleotides, 4 to 8 nucleotides, 4 to 7 nucleotides, 4 to 6 nucleotides, or 4 to 5 nucleotides. In some embodiments, the engineered nucleic acid strand comprises a nucleotide subsequence having a length of 11 to 10 nucleotides, 11 to 9 nucleotides, 11 to 8 nucleotides, 11 to 7 nucleotides, 11 to 6 nucleotides, or 11 to 5 nucleotides. In some embodiments, the engineered nucleic acid strand comprises a nucleotide subsequence having a length of 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, a nucleic acid strand comprises one or more nucleotide subsequences. In some embodiments, the engineered nucleic acid strand comprises 1-10 subsequences, 1-100 subsequences, 1-500 subsequences, or 1-1000 subsequences. In some embodiments, the engineered nucleic acid strand comprises 1, 2, 3, 4, 5, 6, 7, 8, 9, 10, 20, 30, 40, 50, 60, 70, 80, 90, 100, 200, 300, 400, 500, 600, 700, 800, 900, 1000, or more nucleic acid subsequences.

In some embodiments, the nucleic acid strand has a GC-content of 20% to 60% for each subsequence having a length of at least 10, 20, 30, 40 or 50 nucleotides. In some embodiments, the nucleic acid subsequence having a length of at least 10, 20, 30, 40 or 50 nucleotides has a GC-content of 20% to 60%, 20% to 50%, 20% to 40%, or 20% to 30%. In some embodiments, the nucleic acid subsequence having a length of at least 10, 20, 30, 40 or 50 nucleotides has a GC-content of 25% to 60%, 30% to 60%, 40% to 60%, or 50% to 60%. In some embodiments, the nucleic acid subsequence having a length of at least 10, 20, 30, 40 or 50 nucleotides has a GC-content of 20%, 25%, 30%, 35%, 40%, 45%, 50%, 55%, or 60%.

In some embodiments, a nucleic acid strand has a length of at least 100, at least 200, at least 300, at least 400, at least 500, at least 600, at least 700, at least 800, at least 900, at least 1000, at least 1500, at least 2000, at least 3000, at least 4000, or at least 5000 nucleotides. In some embodiments, a nucleic acid strand may have a length of 100-100000, 100-50000, 100-25000, 100-10000, 100-5000, 100-4000, 100-3000, 100-2000, 100-1500, 100-1000, 100-500, or 100-250 nucleotides. In some embodiments, a nucleic acid strand is shorter than 100, shorter than 90, shorter than 80, shorter than 70, shorter than 60, or shorter than 50 nucleotides. In some embodiments, a nucleic acid strand has a length of 100, 500, 1000, 1500, 2000, 2500, 3000, 3500, 4000, 4500 or 5000 nucleotides. For example, a nucleic acid strand having a length of 1000 nucleotides is shown in FIG. 1.

A nucleic acid strand may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine. In some embodiments, the engineered nucleic acid strand is a DNA strand.

It should be understood that the nucleic acid sequences of the present disclosure are engineered to minimize or eliminate kinetic barriers to self-assembly. Thus, the nucleic acid strand may be referred to as an "engineered nucleic acid strand" or an "engineered scaffold strand." An engineered nucleic acid strand is a contiguous sequence of nucleic acids comprising less than 10% of one of C, G, T or A nucleotides and nucleotide sequences having minimal (e.g., less than 4, less than 3, less than 2) repetitive subsequences.

Nucleic acid sequences of the present disclosure may include backbone modifications, base modifications, and/or sugar modifications. Non-limiting examples of these modifications are provided herein.

In some embodiments, a nucleic acid strand of the present disclosure may comprise a backbone other than a phosphodiester backbone. For example, an engineered nucleic acid strand, in some embodiments, may comprise phosphoramide, phosphorothioate, phosphorodithioate, O-methylphophoroamidite linkages, peptide nucleic acids or a combination of any two or more of the foregoing linkages. An engineered nucleic acid strand may be single-stranded (ss) or double-stranded (ds), as specified, or an engineered nucleic acid strand may contain portions of both single-stranded and double-stranded sequence. In some embodiments, an engineered nucleic acid strand contains portions of triple-stranded sequence, or other non-Watson-Crick base pairing such as G-quartets, G-quadruplexes, and i-motifs.

In some embodiments, a nucleic acid strand may comprise a sugar modification. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$) alkyl-ribose is 2'-O-methylribose, 2'-O($C_2$-$C_6$)alkenyl-ribose, 2'-[O—($C_1$-$C_6$)alkyl-O($C_1$-$C_6$)alkyl]-ribose, 2'-$NH_2$-2'-deoxyribose, 13-D-xylo-furanose, a-arabinofuranose, 2,4-dideoxy-3-D-erythro-hexo-pyranose, and carbocyclic and/or open-chain sugar analogs and/or bicyclosugar analogs.

In some embodiments, a nucleic acid strand may comprise a base modifications. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-($C_2$-$C_6$) alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide).

Nucleic Acid Nanostructure

Nucleic acid nanostructures, as provided herein, are two-dimensional or three-dimensional structures that self-assemble into a predesigned shape by hybridization of a plurality of shorter staple oligonucleotides to a longer scaffold nucleic acid strand. In order to self-assemble, nuclei acid nanostructures must overcome kinetic barriers to assembly including intramolecular base pairing and secondary structure formation. The fundamental principle for nanostructure assembly, as provided herein, is engineering nucleic acid sequences in a way that minimizes or eliminates secondary structure formation and undesired/unintended intermolecular interactions, thereby minimizing or eliminating kinetic barriers to assembly. More specifically, nucleic acid sequences disclosed herein have primarily three different types of nucleotides (e.g., A, T and C, or A, T and G) and have minimal subsequence repeats.

Nucleic acid "nanostructures" produced in accordance with the present disclosure are typically nanometer-scale structures (e.g., having lengths of 1 to 1000 nanometers). In some embodiments, the term "nanostructure" herein may refer to micrometer-scale structures (e.g., assembled from more than one nanometer-scale or micrometer-scale structure). In some embodiments, a nanostructure has a diameter of greater than 500 nm or greater than 1000 nm. In some embodiments, a nanostructure has a length scale of 1 micrometer to 2 micrometers. In some embodiments, a nanostructure has a length scale of 10 to 500 nm, 10 to 450 nm, 10 to 400 nm, 10 to 350 nm, 10 to 300 nm, 10 to 250 nm, 10 to 200 nm, 10 to 150 nm, 10 to 100 nm, 10 to 50 nm, or 10 to 25 nm. In some embodiments, the nanostructure has a diameter of 500 to 450 nm, 500 to 400 nm, 500 to 350 nm, 500 to 300 nm, 500 to 250 nm, 500 to 200 nm, 500 to 150 nm, 500 to 100 nm, 500 to 50 nm, or 500 to 25 nm. In some embodiments, the nanostructure has a diameter of 10, 25, 50, 75, 100, 150, 200, 250, 300, 350, 400, 450, or 500 nm.

A plurality of oligonucleotides anneals to the nucleic acid strand through nucleotide base pairing to fold the nanostructure into an arbitrary shape. In some embodiments, the plurality of oligonucleotides is a plurality of DNA oligonucleotides. In some embodiments, the plurality of oligonucleotides comprises 10-2000 oligonucleotides, 10-1500 oligonucleotides, 10-1000 oligonucleotides, 10-500 oligonucleotides, 10-250 oligonucleotides, 10-100 oligonucleotides, 10-50 oligonucleotides or 10-25 oligonucleotides. In some embodiments, the plurality of oligonucleotides comprises 2000-1500 oligonucleotides, 2000-1000 oligonucleotides, 2000-500 oligonucleotides, 2000-250 oligonucleotides, 2000-100 oligonucleotides, 2000-50 oligonucleotides, or 2000-25 oligonucleotides. In some embodiments, the plurality of oligonucleotides comprises 500-600 oligonucleotides, 600-700 oligonucleotides, 700-800 oligonucleotides, 800-900 oligonucleotides, 1000-1100 oligonucleotides, 1100-1200 oligonucleotides, 1200-1300 oligonucleotides, 1300-1400 oligonucleotides, or 1400-1500 oligonucleotides. In some embodiments, the plurality of oligonucleotides comprises 10, 25, 50, 100, 250, 500, 1000, 1500, or 2000 oligonucleotides.

Figure 4:
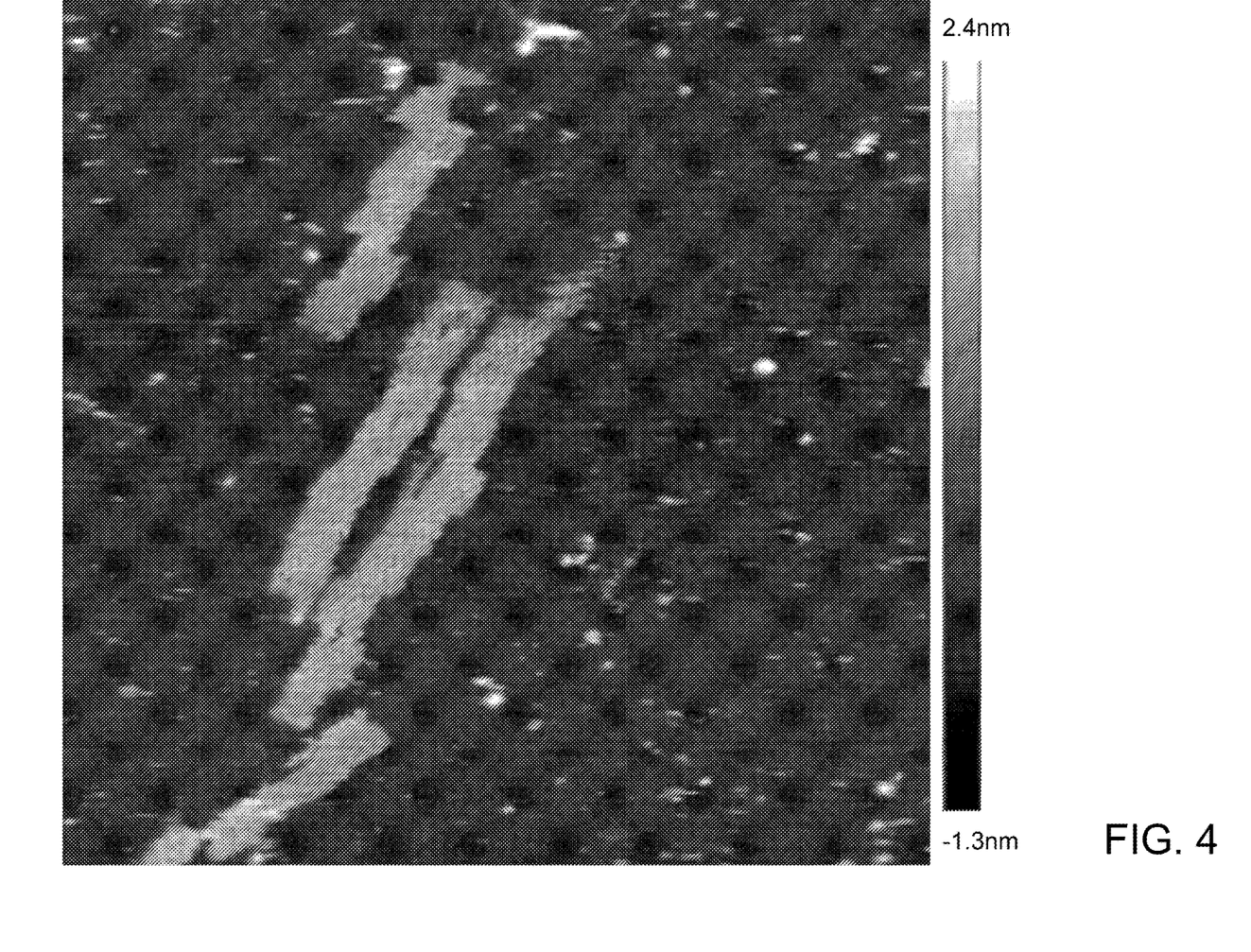
FIG. 4 shows DNA origami assembled from a 1000 base long DeBruijn-derived scaffold sequence and a corresponding staple set. The scaffold and staple strands were mixed together and incubated at room temperature for five minutes in 1×TE buffer supplemented with 10 mM $Mg^{++}$. Image size: 1 μm×1 μm.

The nucleic acid nanostructures produced in accordance with the present disclosure may take any shape or form. For example, a rectangular DNA nanostructure comprising a nucleic acid strand and a plurality of oligonucleotides was assembled as shown in FIG. 4. Using the methods disclosed herein, it is possible to predesign and assemble nanostructures comprising various shapes, forms, and sizes.

In some embodiments, the nucleic acid nanostructure comprises a nucleic acid strand having a length of at least 100 nucleotides and having a nucleotide sequence that comprises less than 10% of one of C, G, T or A nucleotides; and a plurality of oligonucleotides, wherein each oligonucleotide is at least partially complementary to and at least partially bound to the nucleic acid strand. Nucleic acid strand embodiments of a have been disclosed herein.

It should be also understood that the nucleic acid sequences may be designed manually or by computer means based on the teachings provided herein. In some embodiments, the nucleic acid sequences are DeBruijn derived nucleic acid sequences.

The nucleic acid structures may be isolated and/or purified. Isolation, as used herein, refers to the physical separation of the desired entity (e.g., nucleic acid structures, etc.) from the environment in which it was generated. The isolation may be partial or complete.

Isolation of the nucleic acid structure may be carried out by running a hybridization reaction mixture on a gel and isolating nucleic acid structures that migrate at a particular molecular weight and are thereby distinguished from the nucleic acid substrates and the spurious products of the hybridization reaction. As another example, isolation of nucleic acid structures may be carried out using a buoyant density gradient, sedimentation gradient centrifugation, or through filtration means.

Nucleic Acid Nanostructure Assembly

Provided herein, in some aspects, are methods of minimizing or eliminating kinetic barriers through sequence design, thereby providing for a means of rapid assembly of nucleic acid nanostructures at room temperature.

In some embodiments, a method of producing a nucleic acid nanostructure comprises incubating, in a reaction vessel, (a) a nucleic acid strand having a length of at least 100 nucleotides and having a nucleotide sequence that comprises less than 10% of one of C, G, T or A nucleotides; and (b) a plurality of oligonucleotides, wherein each oligonucleotide is at least partially complementary to and at least partially bound to the nucleic acid strand, under conditions that result in binding of the oligonucleotides to the nucleic acid strand to form a nucleic acid nanostructure.

In some embodiments, the conditions include incubating nucleic acid strand and plurality of oligonucleotides for at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, or at least 60 minutes. In some embodiments, the conditions include incubating nucleic acid strand and plurality of oligonucleotides for more than 1 hour, more than 2 hours, more than 4 hours, more than 8 hours, more than 24 hours, more than 48 hours, or more than 72 hours.

In some embodiments, the conditions include incubating nucleic acid strand and plurality of oligonucleotides at room temperature. In some embodiments, the conditions include incubating nucleic acid strand and plurality of oligonucleotides isothermally at a temperature ranging from 4° C. to 10° C., 4° C. to 20° C. 4° C. to 30° C., 4° C. to 40° C., 4° C. to 50° C., 4° C. to 60° C., or 4° C. to 70° C. In some embodiments, the conditions include incubating nucleic acid strand and plurality of oligonucleotides isothermally at 20° C., 21° C., 22° C., 23° C., 24° C., 25° C., 26° C., 27° C., 28° C., 29° C., 30° C.

In some embodiments, a nucleic acid strand and complementary oligonucleotides are combined in a reaction vessel such as, but not limited to a tube, a well, a vial, and the like. In some embodiments, a reaction vessel is incubated in any constant temperature environment. In some embodiments, a reaction vessel is incubated in a PCR machine.

In an exemplary method, a rectangular nanostructure comprising a nucleic acid strand having a length of 1000 nucleotides and a plurality of oligonucleotides were incubated in buffer containing 1×TE and 10 mM $Mg^{2+}$ and assembled in only 5 minutes at room temperature (FIG. 2).

Applications and Uses

It should be understood that while the nucleic acid nanostructures themselves (the base structure) typically consist of a engineered nucleic acid strand and a plurality of oligonucleotides folded into a desired shape, the nanostructures may comprise agents or other molecules that are added to or attached to the folded nanostructure, as described elsewhere herein. For example, in some embodiments, nanostructures of the present disclosure may be decorated with therapeutic moieties (e.g., antibodies) that are more stable at room temperature and, thus the therapeutic moieties maintain stability during rapid room temperature assembly which lacks exposure to high annealing temperatures.

The nanostructures of the present disclosure may be used as therapeutics, or therapeutic delivery vehicles, for a multitude of biomedical applications, including cancer therapy and immunotherapy. Nanostructures can be used, for example, to organize various agents (e.g., proteins, such as antibodies) with controlled spatial distance. In another example, nanostructures can be used to encapsulate therapeutic agents (e.g., antibodies) and deploy them specifically in the vicinity of a tissue in vivo (e.g., a tumor) using, for example, targeting peptides (e.g., tumor targeting peptides).

The nanostructures may contain any agent that is intended for use in vivo and/or in vitro, in a biological or non-biological application. For example, an agent may be any atom, molecule, or compound that can be used to provide benefit to a subject (including without limitation prophylactic or therapeutic benefit) or that can be used for diagnosis and/or detection (for example, imaging) in vivo, or that may be used for effect in an in vitro setting (for example, a tissue or organ culture, a clean-up process, and the like). The agents may be without limitation therapeutic agents and diagnostic agents. Any agent may be incorporated in a disclosed nanostructure provided that it can be assembled and/or loaded into the nanostructure.

The agent may be without limitation a chemical compound including a small molecule, a protein, a polypeptide, a peptide, a nucleic acid, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form. More than one agent or more than one type of agent may be assembled and/or loaded in the nanostructure.

A variety of agents that are currently used for therapeutic or diagnostic purposes include without limitation imaging agents, immunomodulatory agents such as immunostimulatory agents and immunoinhibitory agents (e.g., cyclosporine), antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, analgesics, opioids, enzyme inhibitors, neurotoxins, hypnotics, anti-histamines, lubricants, tranquilizers, anti-convulsants, muscle relaxants, anti-Parkinson agents, anti-spasmodics, muscle contractants including channel blockers, miotics and anti-cholinergics, anti-glaucoma compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

In some embodiments, an agent is a diagnostic agent such as an imaging agent. As used herein, an imaging agent is an agent that emits signal directly or indirectly thereby allowing its detection in vivo. Imaging agents such as contrast agents and radioactive agents can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include 201Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203Pb, and 11In; imaging agents for in vivo fluorescence imaging such as fluorescent dyes or dye-conjugated nanoparticles.

Nucleic Acid Nanostructure Kit

In one aspect, the present disclosure provides a kit for assembling, at room temperature, a nanostructure comprising a nucleic acid strand having three different nucleotides and a plurality of oligonucleotides.

A kit may contain one or more components related to assembly of a nanostructure at room temperature. In some embodiments, a kit comprises a nucleic acid "scaffold" strand as described herein. In some embodiments, a kit comprises a plurality of oligonucleotides as presently disclosed, wherein each oligonucleotide is at least partially complementary to and at least capable of partially binding to the nucleic acid strand. In some embodiments, a kit component comprises instructions for assembling a nanostructure as described herein. In some embodiments, the instructions relate to composition of one or more kit components and/or methods of use of nanostructures.

The components of the kit may be provided in any suitable form. In some embodiments, components are provided as liquid solutions or as dried powders. In some embodiments, components provided as a dry powder may be reconstituted by the addition of a suitable buffer, which may also be provided. In some embodiments, the buffer comprises magnesium, sodium, monovalent cations, and/or divalent cations. For example, a nanostructure was assembled in buffer comprising 1×TE buffer supplemented with 10 mM $Mg^{2+}$. In some embodiments, components provided as liquid solutions may be concentrated or ready to use.

EXAMPLE

Eliminating Kinetic Barriers Through a Sequence Design Allows Rapid Assembly of DNA Origami at Room Temperature DNA origami [3] is a robust and programmable technique to make DNA nanostructures. A key use of DNA origami structures has been as nanoscale breadboards that organize components like small proteins, nanoparticles, small molecules and other DNA strands. Typical DNA origami assembly requires that the scaffold strand be annealed with staple strands in the appropriate buffer. The high temperatures (>80 C) used in this process are not always compatible with temperature-sensitive components or contexts. In response, there have been attempts to isothermally fold DNA. Studies have shown that DNA origami can assemble isothermally if held at temperatures around 60 C [4, 5], or at room temperature by using denaturing agents [1, 2]. However, rapid assembly of DNA origami at room temperature without the use of denaturing agents, which can be toxic or have other unintended consequences, has not been achieved.

A rectangular DNA origami was assembled from a 1000 base long DeBruijn-derived scaffold sequence and a corresponding staple set. The origami assembled isothermally in as little as five minutes at temperatures ranging from 25° C. to 50° C.

Traditional DNA origami designs are faced with prohibitive kinetic barriers to assembly at room temperature. Heating, or using denaturing agents, helps overcome these barriers. An alternate approach was taken. Computational sequence design was used to eliminate prohibitive kinetic barriers and thus assemble DNA origami at room temperature in as little as five minutes.

The key contributions to kinetic barriers are: secondary structure of the scaffold, secondary structure of staple strands, and undesired staple-staple interactions. These issues were circumvented by the use of a three letter code.

The scaffold sequence was chosen from the three letter alphabet {A, T, C} and the staple sequences from the complementary alphabet {A, T, G}. Mfold and NUPACK analysis of the resulting sequences showed dramatic reduction in predicted secondary structure (FIG. 1) and unintended staple-staple interactions through this strategy. A potential drawback of a three letter code is reduced sequence diversity. A four letter code affords $4^8 \approx 65000$ distinct 8-mers while a three letter code affords only $3^8 \approx 6500$. Thus, a poorly chosen three letter scaffold sequence could have poor sequence diversity that results in unintended staple-scaffold interactions, resulting in kinetic barriers to assembly. Such "poor choices" were minimized by using DeBruijn sequences to maximize sequence diversity and prevent unintended staple-scaffold interactions. A DeBruijn sequence S of order n over the three letter alphabet {A, T, C} is a sequence where every possible subsequence of length n appears exactly once. DeBruijn sequences can be generated computationally in time linear in the length of the sequence. DeBruijn sequences were adapted to filter out degenerate subsequences and to ensure that the C content was evenly distributed across the sequence. The resulting sequence is considered to be DeBruijn-derived and is selected as the scaffold sequence (FIG. 2).

The following example illustrates derivation of DeBruijn sequences. Given an alphabet of size k (i.e. there are k letters in the alphabet; for example, {A, T, C} is a 3-letter alphabet) there are a possible $k^n$ distinct words of length n. For example, the alphabet {A, T, C} has $3^2=9$ distinct words of length 2: AA, AT, AC, TA, TT, TC, CA, CT, CC.

The number of subsequences is calculated from the sequence length (l). Consider a sequence (S) of length (l), wherein S has l−n+1 subsequences of length n. For example, the sequence ATTTATACCTATTA (SEQ ID NO: 1) has length 14 and has 14-3+1=12 subsequences of length 3, namely ATT, TTT, TTA, TAT, ATA, TAC, ACC, CCT, CTA, TAC, ATT, TTA which are obtained by taking a window of length 3 and sliding it along the sequence. Note that not all subsequences are necessarily unique. For instance, the subsequence ATT and TTA both occur twice, and we say they are repeated.

Sequence repeats are minimized according to the following: a k-ary DeBruijn sequence of order n is a sequence over a k letter alphabet where every subsequence of size n occurs exactly once. There are $k^n$ such subsequences and hence the length of the DeBruijn sequence is $l=k^n+n-1$.

Given a sequence of length l over a k letter alphabet, we minimize sequence repeats by the following procedure:
  Choose the smallest positive integer n that satisfies $k^n+n-1<=l$
  Compute a k-ary DeBruijn sequence of order n by taking an Eulerian tour of a DeBruijn graph (this is a standard algorithm)
  Choose any subsequence of length l of this DeBruijn sequence. This is our target sequence. Note that our target sequence has the property that all subsequences of length n or larger occur at most once. That is, no subsequences of length n or larger are repeated.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The term "or" is generally employed in its sense including "and/or" unless the content clearly dictates otherwise.

It should be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended (including but not limited to). Only the transitional phrases "consisting of" and "consisting essentially of" shall be closed or semi-closed transitional phrases, respectively, as set forth in the United States Patent Office Manual of Patent Examining Procedures, Section 2111.03. It should also be understood that all open-ended transitional phrases may be substituted with closed or semi-closed transitional phrases. Thus, the term "comprising" may be substituted with "consisting of" or "consisting essentially of."

REFERENCES

[1] Ralf Jungmann, Tim Liedl, Thomas L. Sobey, William Shih, and Friedrich C. Simmel. Isothermal assembly of DNA origami structures using denaturing agents. Journal of the American Chemical Society, 130(31):10062-10063, 2008. PMID: 18613687.
[2] Andreas Kopielski, Anne Schneider, Andrea Csaki, and Wolfgang Fritzsche. Isothermal DNA origami folding: avoiding denaturing conditions for one-pot, hybrid-component annealing. Nanoscale, 7:2102-2106, 2015.
[3] Paul Rothemund. Folding DNA to Create Nanoscale Shapes and Patterns. Nature, 440:297-302, 2006.
[4] Jean-Philippe J. Sobczak, Thomas G. Martin, Thomas Gerling, and Hendrik Dietz. Rapid folding of DNA into nanoscale shapes at constant temperature. Science, 338 (6113):1458-1461, 2012.
[5] Jie Song, Zhao Zhang, Shuai Zhang, Lei Liu, Qiang Li, Erqing Xie, Kurt Vesterager Gothelf, Flemming Besenbacher, and Mingdong Dong. Isothermal hybridization kinetics of DNA assembly of two-dimensional DNA origami. Small, 9(17):2954-2959, 2013.

What is claimed is:

1. A nucleic acid nanostructure comprising:
   (a) a deoxyribonucleic acid (DNA) strand having a length of at least 100 nucleotides and having a nucleotide sequence that comprises less than 10% of one of C, G, T or A nucleotides; and
   (b) 10-2000 oligonucleotides, wherein each oligonucleotide is at least partially complementary to and at least partially bound to the DNA strand.

2. The nucleic acid nanostructure of claim 1, wherein the nucleotide sequence comprises greater than 90% of A, T and C nucleotides and less than 10% of G nucleotides.

3. The nucleic acid nanostructure of claim 1, wherein the nucleotide sequence comprises greater than 90% of A, T and G nucleotides and less than 10% of C nucleotides.

4. The nucleic acid nanostructure of claim 1, wherein the nucleotide sequence comprises less than 5% of one of C, G, T or A nucleotides.

5. The nucleic acid nanostructure of claim 1, wherein the nucleotide sequence comprises 1-5% of one of C, G, T or A nucleotides.

6. The nucleic acid nanostructure of claim 1, wherein the nucleotide sequence comprises nucleotide subsequences, each of which is present only once in the DNA strand.

7. The nucleic acid nanostructure of claim 6, wherein the nucleotide subsequences have a length of 5 to 10 nucleotides.

8. The nucleic acid nanostructure of claim 1, wherein the DNA strand has a length of at least 500 nucleotides.

9. The nucleic acid nanostructure of claim 1, wherein the DNA strand has a length of at least 1000 nucleotides.

10. The nucleic acid nanostructure of claim 9, wherein the DNA strand has a length of 100-100,000 nucleotides.

11. The nucleic acid nanostructure of claim 1, wherein the nucleic acid nanostructure is three-dimensional.

12. A nucleic acid nanostructure of comprising:
   (a) a deoxyribonucleic acid (DNA) strand having a length of at least 100 nucleotides and having a nucleotide sequence that comprises less than 10% of one of C, G, T or A nucleotides; and
   (b) a plurality of oligonucleotides, wherein each oligonucleotide is at least partially complementary to and at least partially bound to the DNA strand, wherein the nanostructure is a three-dimensional DNA origami structure and has a diameter of 10-500 nm.

13. A kit comprising
   (a) a deoxyribonucleic acid (DNA) strand having a length of at least 100 nucleotides and having a nucleotide sequence that comprises less than 10% of one of C, G, T or A nucleotides; and
   (b) 10-2000 oligonucleotides, wherein each oligonucleotide is at least partially complementary to and at least partially bound to the DNA strand.

14. A method of producing a DNA origami nanostructure, comprising
   incubating, in a reaction vessel,
   (a) a deoxyribonucleic acid (DNA) strand having a length of at least 100 nucleotides and having a nucleotide sequence that comprises less than 10% of one of C, G, T or A nucleotides, and
   (b) a plurality of oligonucleotides, wherein each oligonucleotide is at least partially complementary to the DNA strand,
   under conditions that result in binding of the oligonucleotides to the DNA strand to form a DNA origami nanostructure.

* * * * *

SEQUENCE LISTING

<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 1
atttatacct atta